(12) United States Patent
Puno et al.

(10) Patent No.: US 8,486,083 B2
(45) Date of Patent: Jul. 16, 2013

(54) METHODS AND INSTRUMENTATION FOR INSERTING INTERVERTEBRAL GRAFTS AND DEVICES

(75) Inventors: Rolando M. Puno, Prospect, KY (US); Bret M. Berry, Sandy, UT (US); W. Scott Gareiss, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 817 days.

(21) Appl. No.: 12/590,948

(22) Filed: Nov. 17, 2009

(65) Prior Publication Data

US 2010/0069914 A1   Mar. 18, 2010

Related U.S. Application Data

(63) Continuation of application No. 10/764,621, filed on Jan. 26, 2004, now Pat. No. 7,625,379.

(51) Int. Cl.
*A61B 17/88* (2006.01)

(52) U.S. Cl.
USPC .......................................... 606/99; 606/86 A

(58) Field of Classification Search
USPC ............................ 606/240, 90, 99, 105, 86 A; 623/17.11–17.16
See application file for complete search history.

(56) References Cited

U.S. PATENT DOCUMENTS

| | | | |
|---|---|---|---|
| 3,486,505 A * | 12/1969 | Morrison | ........................ 606/90 |
| 4,386,603 A | 6/1983 | Mayfield | |
| 4,736,738 A | 4/1988 | Lipovsek et al. | |
| 4,758,159 A | 7/1988 | Weissman | |
| 4,898,161 A | 2/1990 | Grundei | |
| 4,955,885 A | 9/1990 | Meyers | |
| 4,957,495 A | 9/1990 | Kluger | |
| 5,122,130 A | 6/1992 | Keller | |
| 5,192,327 A | 3/1993 | Brantigan | |
| 5,235,966 A | 8/1993 | Jamner | |
| 5,431,658 A * | 7/1995 | Moskovich | ..................... 606/99 |
| 5,505,732 A | 4/1996 | Michelson | |
| 5,571,109 A | 11/1996 | Bertagnoli | |
| 5,599,279 A | 2/1997 | Slotman et al. | |
| 5,697,889 A | 12/1997 | Slotman et al. | |
| 5,722,977 A | 3/1998 | Wilhelmy | |
| 5,944,658 A | 8/1999 | Koros et al. | |

(Continued)

FOREIGN PATENT DOCUMENTS

| | | |
|---|---|---|
| EP | 0531710 | 3/1993 |
| EP | 0637439 | 2/1995 |
| EP | 1295578 | 3/2003 |
| EP | 1323396 | 7/2003 |

OTHER PUBLICATIONS

Synthes, SynCage Surgical Technique; Mathys Medical Ltd—Osteosynthesis., pp. 1-24, Guterstrasse 5, P.O. Box CH-2544 Bettlach, Switzerland.

*Primary Examiner* — Eduardo C Robert
*Assistant Examiner* — David Comstock

(57) ABSTRACT

Instruments for inserting an implant in a space between adjacent bony portions include upper and lower guide members separated by a spreader with the implant positioned forwardly of the spreader. The spreader is movable forwardly between the guide members with a drive member to position the implant in a space between the bony portions. The spreader contacts the adjacent bony portions to facilitate withdrawal of the inserter instrument when the implant is positioned in the space.

20 Claims, 16 Drawing Sheets

U.S. PATENT DOCUMENTS

| | | | |
|---|---|---|---|
| 6,004,326 A | 12/1999 | Castro et al. | |
| 6,083,225 A | 7/2000 | Winslow et al. | |
| 6,096,038 A | 8/2000 | Michelson | |
| 6,159,215 A | 12/2000 | Urbahns et al. | |
| 6,174,311 B1 | 1/2001 | Branch et al. | |
| 6,179,873 B1 | 1/2001 | Zientek | |
| 6,224,599 B1 | 5/2001 | Baynham et al. | |
| 6,224,607 B1 | 5/2001 | Michelson | |
| 6,261,296 B1 | 7/2001 | Aebi et al. | |
| 6,270,498 B1 | 8/2001 | Michelson | |
| 6,332,887 B1 | 12/2001 | Knox | |
| 6,395,034 B1 | 5/2002 | Suddaby | |
| 6,436,101 B1 | 8/2002 | Hamada | |
| 6,478,800 B1 * | 11/2002 | Fraser et al. | 606/99 |
| 6,514,260 B1 | 2/2003 | Zdeblick et al. | |
| 6,565,574 B2 | 5/2003 | Michelson | |
| 6,569,168 B2 | 5/2003 | Lin | |
| 6,595,995 B2 | 7/2003 | Zdeblick et al. | |
| 6,607,559 B2 | 8/2003 | Ralph et al. | |
| 6,610,065 B1 | 8/2003 | Branch et al. | |
| 6,635,060 B2 | 10/2003 | Hanson et al. | |
| 6,641,582 B1 | 11/2003 | Hanson et al. | |
| 6,648,891 B2 | 11/2003 | Kim | |
| 6,652,533 B2 | 11/2003 | O'Neil | |
| 6,663,638 B2 | 12/2003 | Ralph et al. | |
| 6,669,730 B2 | 12/2003 | Ralph et al. | |
| 6,673,113 B2 | 1/2004 | Ralph et al. | |
| 6,887,274 B2 | 5/2005 | Ralph et al. | |
| 7,118,580 B1 * | 10/2006 | Beyersdorff et al. | 606/99 |
| 7,169,153 B2 | 1/2007 | Keller | |
| 2001/0010001 A1 | 7/2001 | Michelson | |
| 2002/0016592 A1 | 2/2002 | Branch et al. | |
| 2002/0058950 A1 | 5/2002 | Winterbottom et al. | |
| 2002/0082695 A1 | 6/2002 | Neumann | |
| 2002/0111687 A1 | 8/2002 | Ralph et al. | |
| 2002/0116009 A1 | 8/2002 | Fraser et al. | |
| 2002/0138078 A1 | 9/2002 | Chappuis | |
| 2002/0177897 A1 | 11/2002 | Michelson | |
| 2003/0014116 A1 | 1/2003 | Ralph et al. | |
| 2003/0028197 A1 | 2/2003 | Hanson et al. | |
| 2003/0040802 A1 | 2/2003 | Errico et al. | |
| 2003/0045884 A1 | 3/2003 | Robie et al. | |
| 2003/0069586 A1 | 4/2003 | Errico et al. | |
| 2003/0069642 A1 | 4/2003 | Ralph et al. | |
| 2003/0069643 A1 | 4/2003 | Ralph et al. | |
| 2003/0078590 A1 | 4/2003 | Errico et al. | |
| 2003/0083664 A1 | 5/2003 | Rogers et al. | |
| 2003/0130737 A1 | 7/2003 | McGahan et al. | |
| 2003/0149438 A1 | 8/2003 | Nichols et al. | |
| 2003/0187448 A1 | 10/2003 | Michelson | |
| 2003/0195517 A1 | 10/2003 | Michelson | |
| 2003/0195520 A1 | 10/2003 | Boyd et al. | |
| 2003/0216810 A1 | 11/2003 | Ralph et al. | |
| 2003/0229358 A1 | 12/2003 | Errico et al. | |
| 2004/0002758 A1 | 1/2004 | Landry et al. | |
| 2004/0024406 A1 | 2/2004 | Ralph et al. | |
| 2004/0143331 A1 | 7/2004 | Errico et al. | |
| 2004/0148027 A1 | 7/2004 | Errico et al. | |
| 2004/0153158 A1 | 8/2004 | Errico et al. | |
| 2004/0158325 A1 | 8/2004 | Errico et al. | |
| 2004/0225295 A1 * | 11/2004 | Zubok et al. | 606/90 |
| 2005/0021040 A1 | 1/2005 | Bertagnoli | |
| 2005/0075643 A1 * | 4/2005 | Schwab et al. | 606/90 |

* cited by examiner

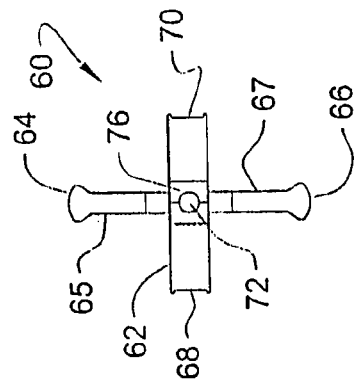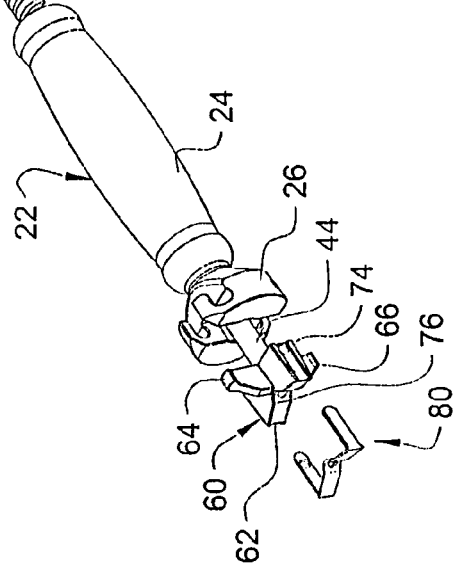

METHODS AND INSTRUMENTATION FOR INSERTING INTERVERTEBRAL GRAFTS AND DEVICES

CROSS-REFERENCE TO RELATED APPLICATIONS

The present application is a continuation of U.S. patent application Ser. No. 10/764,621 filed on Jan. 26, 2004, now U.S. Pat. No. 7,625,379 which is incorporated herein by reference in its entirety.

BACKGROUND

The repair and reconstruction of bony structures is sometimes accomplished by directly fixing adjacent bony portions to each other, such as by a plate. In other instances, bone growth inducing material can be introduced between the adjacent bony portions, which over time results in a solid bony connection. In some instances, the adjacent bony portions are not sufficiently strong to maintain their patency as the bone heals or the bone grows between the adjacent structures through the bone growth inducing material. In these instances, grafts, cages, artificial joints and other implants have been provided to engage the adjacent bony structures to provide additional stability.

One problem, among others, with such implants is associated with positioning the implant in the space between adjacent bony portions. Insertion can be difficult or time consuming if the bony portions are spaced too close together, or if the adjacent tissue, nerves or vasculature impedes access to or placement of the implant in the space between the bony portions. Furthermore, maintenance of distraction of the space during insertion of the implant requires additional instruments in the space or in the operative approach to the space which can make the procedure more invasive and impede access and visibility during implant insertion.

SUMMARY

The invention provides instruments that facilitate placement of an implant between adjacent bony portions.

According to one aspect, the instrument includes a housing and a pair of opposing guide members coupled to the housing. The guide members each include an elongated slot opening between an outer surface and a guide surface of the guide member. A spreader is positioned between the pair of guide members. The spreader includes a central body and a pair of opposite wings extending therefrom slidingly received in the slot of a corresponding one of the pair of guide members. A drive member is coupled to the spreader and operable to forwardly advance the spreader and the implant positioned forwardly of the spreader toward distal ends of the guide members.

According to another aspect, the instrument includes a housing and a pair of opposing guide members coupled to the housing. A spreader is positioned between the pair of guide members. An adapter is releasably coupled to the spreader with a body portion of the adapter along a forward or distal end wall of the spreader. A drive member is coupled to the spreader and is operable to forwardly advance the spreader and adapter with the implant positioned forwardly of the adapter toward distal ends of the guide members. The adapter positions the implant more forwardly relative to the guide members than if the implant were positioned along the forward or distal end wall of the spreader.

In a further aspect, a method for inserting an implant in a space between adjacent bony structures includes: providing an implant inserter with a pair of guide members pivotally coupled to a housing and a spreader between the pair of guide members; pivoting at least one of the pair of guide members away from the other of the pair of guide members to remove a wing of the spreader from a slot of the at least one guide member; positioning an implant between the pair of guide members and forwardly of the spreader; and pivoting the at least one guide member toward the other guide member thereby positioning the wing of the spreader in the slot of the at least one guide member.

In a further aspect, the method includes withdrawing distal support members of the pair of guide members from the space between the implant and the adjacent bony portions by manipulating the drive member to push the wings against the adjacent bony portions and proximally displacing the guide members relative to the bony portions and the implant.

These and other aspects can be discerned from the following written description and accompanying figures.

DESCRIPTION OF THE FIGURES

FIG. 4 is a perspective view of the housing and drive member assembled with a spreader coupled to a distal end of the drive member and an optional adapter exploded from the spreader.

FIG. 5 is a front elevational view of the spreader.

FIG. 6 is a perspective view of the adapter.

DESCRIPTION OF THE ILLUSTRATED EMBODIMENTS

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

An instrument is provided for inserting implants and other devices into a space between adjacent bony portions to support the adjacent bony portions. The inserter instrument can be used with any type of bone support implant, such as artificial joints, spacer devices, and fusion devices, for example. The implants can be made from bone material or any suitable biocompatible metal, plastic, or other material. In one application, the inserter instrument is employed in spinal surgical procedures for inserting an implant in the disc space between adjacent vertebrae. For example, in the illustrated embodiments of FIGS. 10, 12 and 15-18, the adjacent bony portions include first vertebra 220 and second vertebra 222. The vertebrae 220, 222 include a disc space 224 therebetween, which provides a space for insertion of an implant between the adjacent bony portions. The inserter instrument can also be used in corpectomy procedures to position an implant between adjacent vertebrae on either side of one or more removed or partially removed vertebral bodies. The inserter instrument can be used in various approaches to the spine, including posterior, posterior lateral, transforaminal, lateral, anterior lateral, oblique, and anterior approaches. The inserter can also be used in approaches to various regions of the spine, including the lumbar, thoracic and cervical regions. It is contemplated that the inserter instrument can have application in surgical procedures other than spinal surgical procedures to facilitate insertion of an implant between adjacent bony portions.

Figure 1:
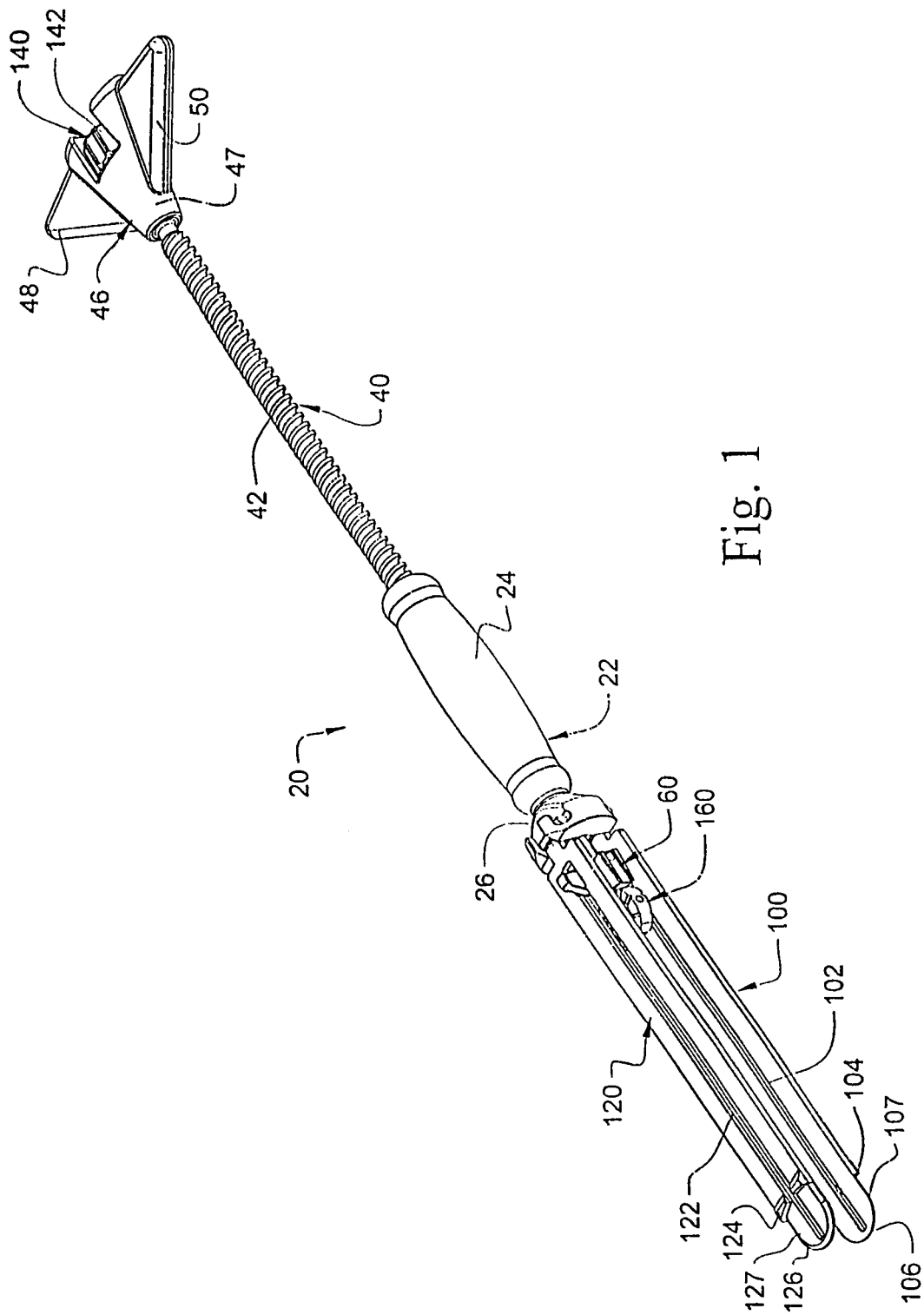
FIG. 1 is a perspective view of an implant inserter instrument.

In FIG. 1 an inserter instrument 20 is shown. Inserter instrument 20 includes an intermediate housing 22 with a drive member 40 extending through and coupled thereto. Drive member 40 includes an implant holder 140 extending therethrough. A pair of guide members 100, 120 are coupled to housing 22 and extend distally therefrom. The distal ends of drive member 40 and implant holder 140 extend in the space between guide members 100, 120. The distal end of drive member 40 engages a spreader 60 positioned between guide members 100, 120. An implant 160 is positioned forwardly of spreader 60. Implant holder 140 extends through spreader 60 and engages implant 160 to facilitate in maintaining its positioning between guide members 100, 120. Spreader 60 is moveable distally or forwardly by manipulating drive member 40 relative to housing 22 to advance drive member 40 forwardly towards distal ends of guide members 100, 120.

The proximal ends of guide members 100, 120 are pivotally attached to housing 22, facilitating loading of the implant 160 and placement of the distal ends of guide members 100, 120 adjacent one another for positioning in the spinal disc space. As spreader 60 pushes implant 160 distally between guide members 100, 120, the distal ends of guide members 100, 120 can separate and thus apply a distraction force to the adjacent vertebrae. The vertebrae are distracted sufficiently to receive implant 160 since the final distraction height is determined by the height of implant 160 between the distal ends of guide members 100, 120.

Figure 2:
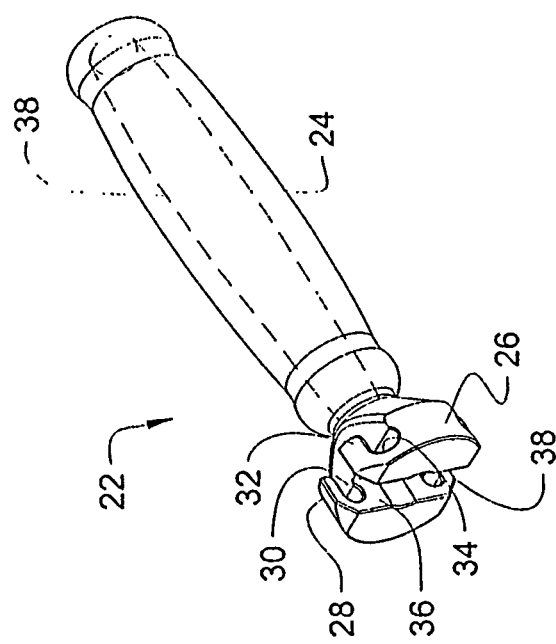
FIG. 2 is a perspective view of a housing of the inserter instrument of FIG. 1.

Further details of the assembly of inserter instrument 20 will be discussed with further reference to FIGS. 2-9. In FIG. 2 there is shown housing 22. Housing 22 includes a drive member engaging portion 24 extending proximally from a distal coupling portion 26. A passage 38 extends through each of drive member engaging portion 24 and coupling portion 26. Coupling portion 26 includes a pair of upwardly and proximally extending upper fingers 28, 32 projecting therefrom. Fingers 28, 32 form proximally opening receptacles 30, 34, respectively, which receive and pivotally capture a guide member 120 (FIG. 14) to coupling portion 26. A slot 36 extends between fingers 28, 32 and along the distally oriented face of coupling member 26 between a pair of opposite lower fingers, only one of which, finger 38, is shown. The lower fingers are identical to upper fingers 28, 32, and pivotally capture lower guide member 100 to coupling member 26.

It should be understood that the terms "upper" and "lower" refer to the orientation of the elements of the instruments in the Figures as shown in an operative approach to the space between adjacent bony portions. The instruments can be rotated or repositioned such that, for example, the lower fingers extend upwardly and guide member 100 is positioned above guide member 120.

Figure 3:
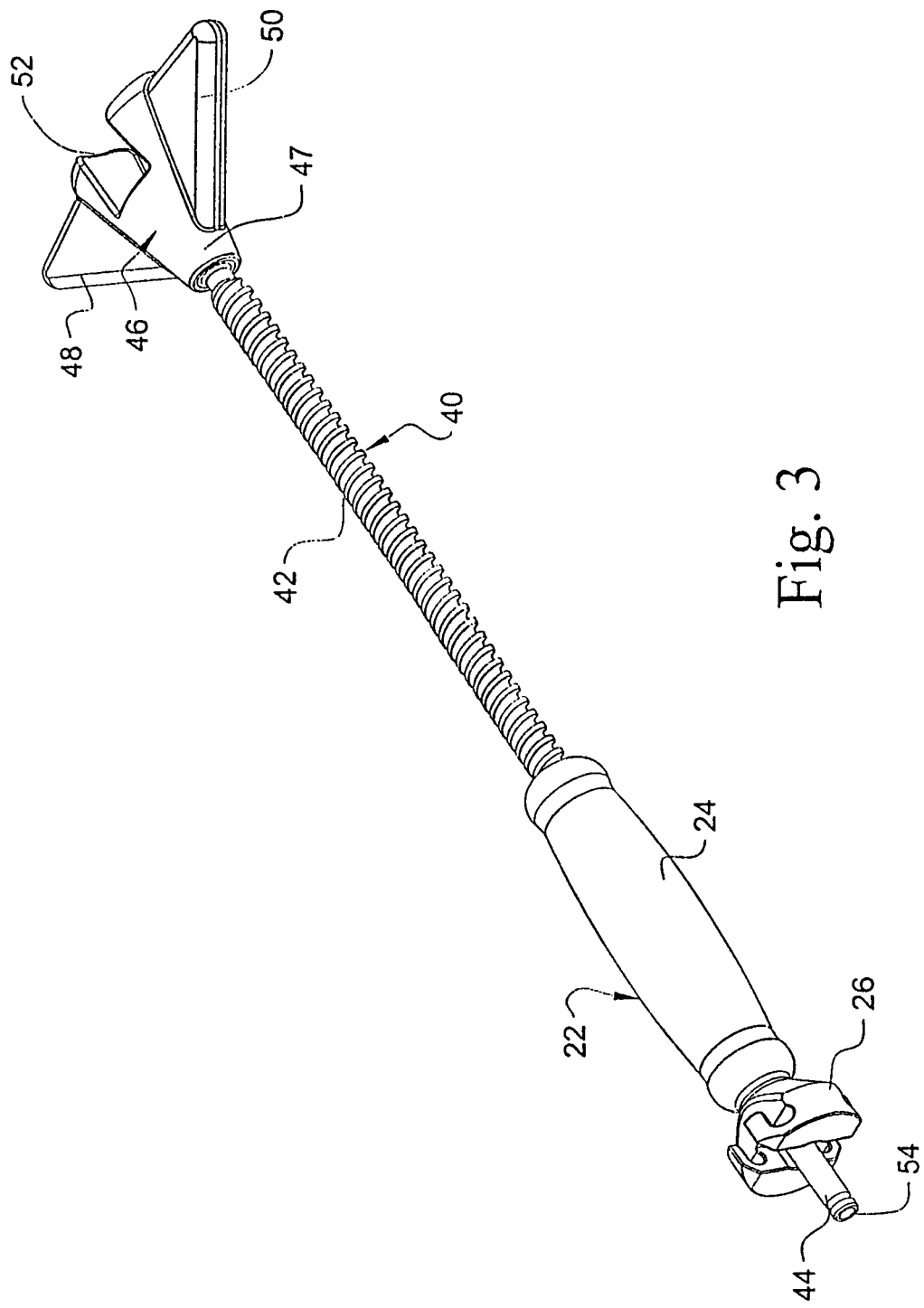
FIG. 3 is a perspective view of the housing of FIG. 2 coupled with a drive member.

Referring to FIG. 3, drive member 40 is coupled to housing 22. In the illustrated embodiment, drive member 40 includes a shaft 42 and proximal handle 46. Handle 46 includes opposite first and second arms 48, 50 extending from a central body portion 47 to facilitate grasping of handle 46. A proximal recess 52 is provided in the central body portion 47 of handle 46. Shaft 42 extends through passage 38 of housing member 22 to a distal end 44. At least a portion of shaft 42 is threaded to threadingly engage an internally threaded portion of passage 38. Accordingly, drive member 40 is movable longitudinally distally and proximally by rotating shaft 42 in housing 22, thereby distally or proximally displacing distal end 44.

In another embodiment, drive member 40 can include a ratchet mechanism. A ratchet bar can be provided along shaft 42, which is moved linearly proximally in housing 22 to distally advance spreader 60 between guide members 100, 120. A handheld trigger-like handle, pinion with a thumbwheel or tool engaging end, or other suitable handle can be provided to effect the linear movement of the ratchet bar. A catch mechanism, either in the handle or housing 22, can maintain the distal positioning of the ratchet bar until it is released, allowing the ratchet bar to be linearly and proximally moved.

In FIG. 4, there is shown spreader 60 attached to distal end 44 of drive member 40. Spreader 60 includes a central body 62 having an upper wing 64 and a lower wing 66 extending therefrom in opposite directions from one another, as shown in FIG. 5. A bore 72 extends centrally through central body 62, and opens at the distal and proximal ends thereof. Distal end 44 of drive member 40 is rotatably received in the trailing or proximal end opening of bore 72. In the illustrated embodiment, distal end 44 includes a circumferential groove to receive a ball plunger in spreader 60. Other suitable rotatable coupling arrangements are also contemplated, such as a C-ring or other suitable connector. Depending on the direction of rotation of drive member 40 about its longitudinal axis, spreader 60 moves distally or proximally without rotation.

Spreader 60 further includes leading or distal end wall that is angled proximally to a central concave receptacle 76. Bore 72 opens into receptacle 76. Spreader 60 further includes lateral sidewalls with grooves 68, 70 formed therein. Each of the sidewalls further includes a detent, such as detent 74 shown in groove 70. The proximally recessed leading or distal end wall of spreader 60 at least partially receives implant 160 positioned forwardly thereof, and resists rotation of the implant 160 as it is advanced between guide members 100, 120.

The recessed distal end wall and grooved lateral walls of spreader 60 further facilitate engagement of an optional adapter 80 to spreader 60. Adapter 80 includes a body 82 having a pair of arms 84, 86 extending proximally therefrom. Body 82 includes a profile that matches the profile of the leading or distal end wall of spreader 60. Body 82 includes a central offset portion 88 adapted to fit within receptacle 76 of spreader 60. Offset portion 88 includes a central hole 90 through which the distal end of implant holder 140 extends to engage implant 160, as discussed further below. Arms 84, 86 include protrusions, such as protrusion 92 on arm 84, extending toward one another. The protrusions releasably engage the adjacent detent in the lateral walls of spreader 60 when adapter 80 is positioned adjacent the leading or distal end wall of spreader 60, engaging adapter 80 thereto.

When coupled to spreader 60, adapter 80 positions the implant more distally relative to guide members 100, 120 by a distance 94 that at least corresponds to the thickness of body 82 and any space between body 82 and the distal end wall of spreader 60. This allows implant 160 to be positioned more distally in the spinal disc space when spreader 60 is advanced to the ends of guide members 100, 120. It is contemplated that multiple adapters 80 can be provided in a set to allow the surgeon to select an adapter providing a desired offset distance.

Figure 7:
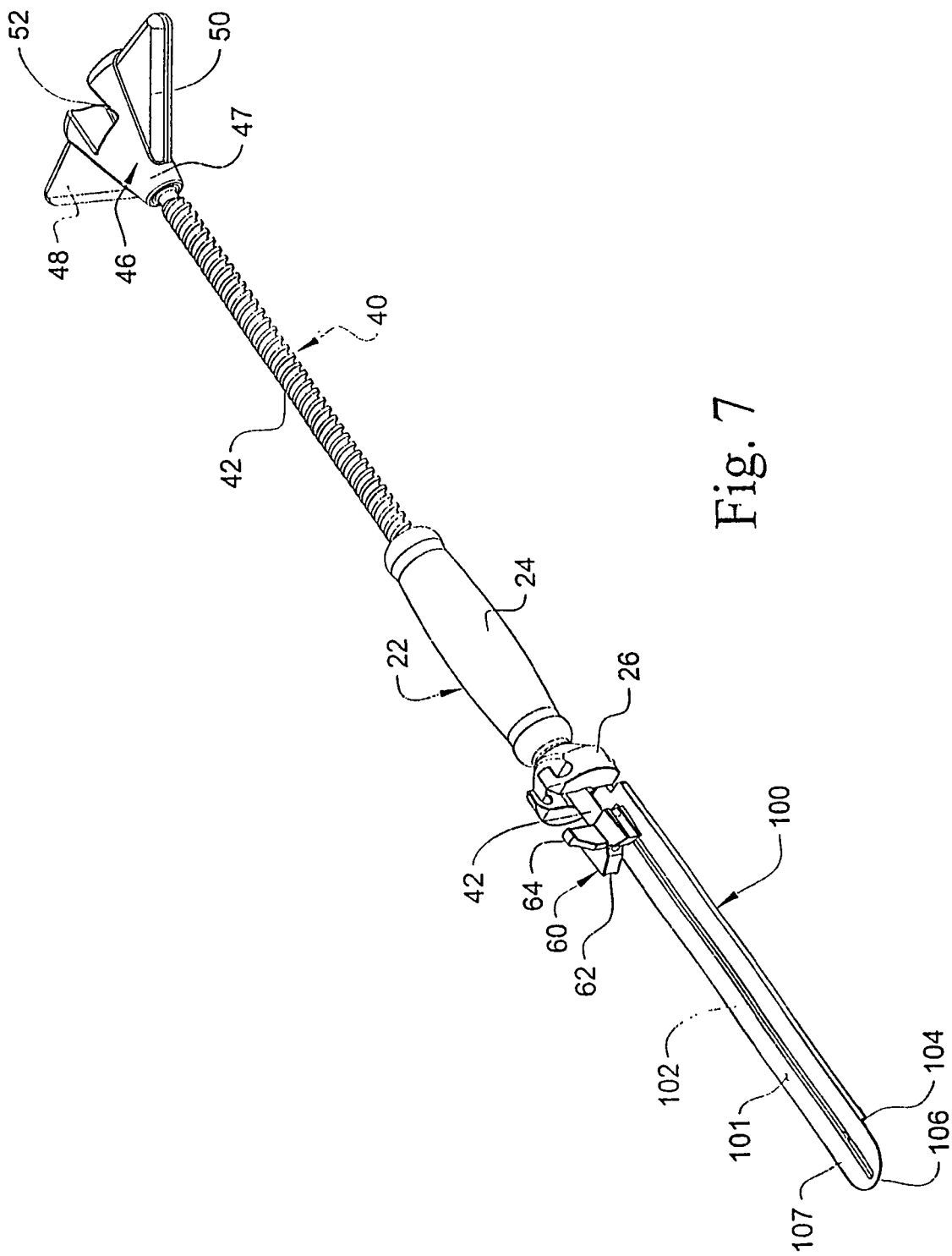
FIG. 7 is a perspective view of the housing, drive member, and spreader assembled with a lower guide member.
Figure 14:
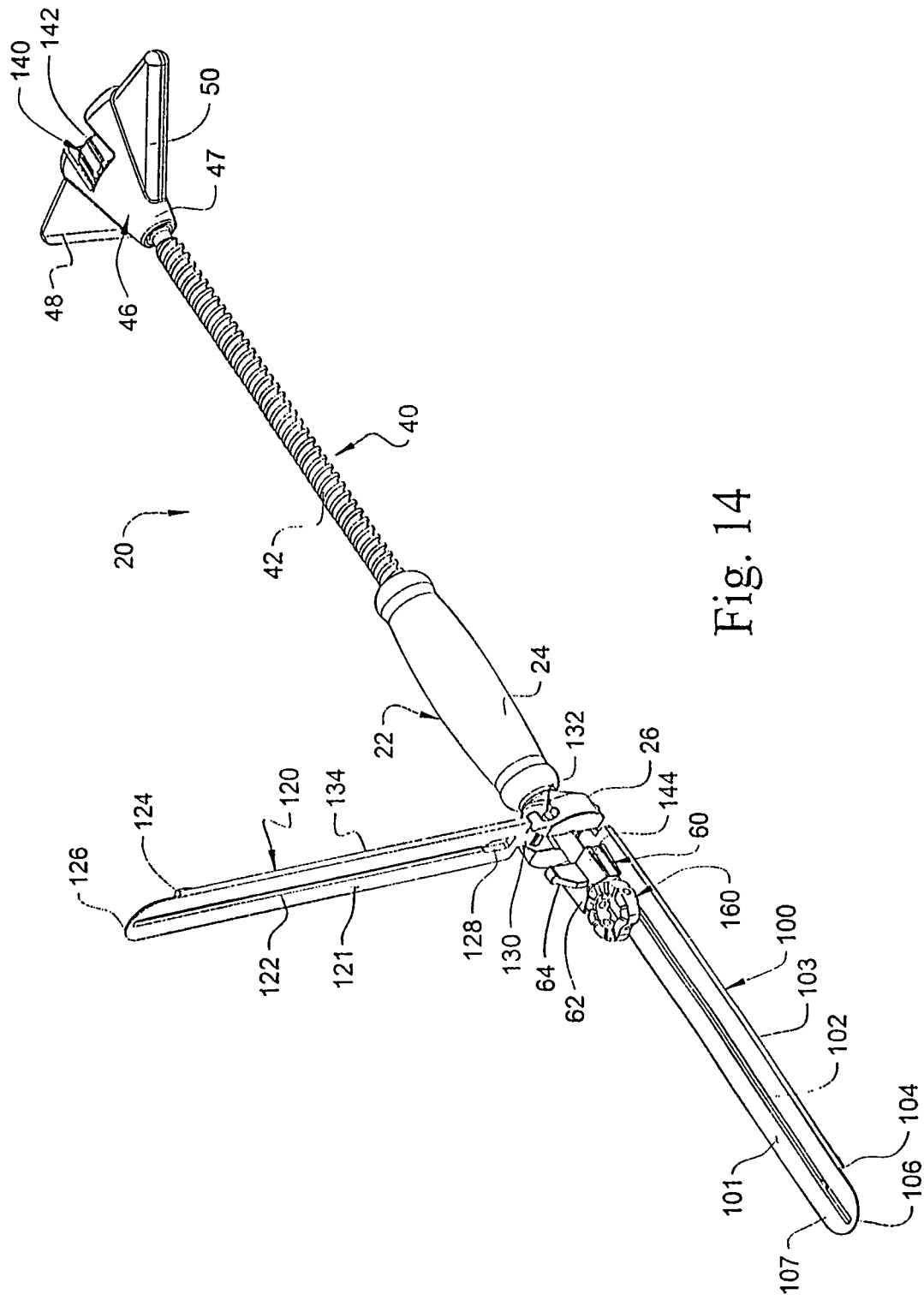
FIG. 14 is a perspective view of implant inserter instrument with an implant being loaded therein.

Referring to FIG. 7, lower guide member 100 is pivotally coupled to coupling portion 26 of housing 22. Upper guide member 120 can be pivotally coupled with the upper fingers 28, 32 of housing 26, as shown in FIG. 14. The proximal ends of guide members include laterally oriented crossbars, such as crossbar 132 shown in FIG. 14. The ends of crossbar 132 are received in corresponding ones of the proximally opening receptacles 30, 34, and reside against the fingers 28, 32, which maintain the guide member 100 in pivotal and removable engagement with housing 26. Lower guide member 100 is similarly pivotally and removably coupled to the opposite, downwardly extending fingers of coupling portion 26. The ability to quickly disassemble guide members 100, 120 allows inserter instrument 20 to be cleaned and sterilized after the surgical procedure is completed. It further allows guide members 100, 120 to be provided in a set of guide members for use with a common housing, drive member and implant holder. For example, the guide members in the set can include various lengths, widths, or abutment member configurations from which the surgeon may select during surgery.

Figure 8:
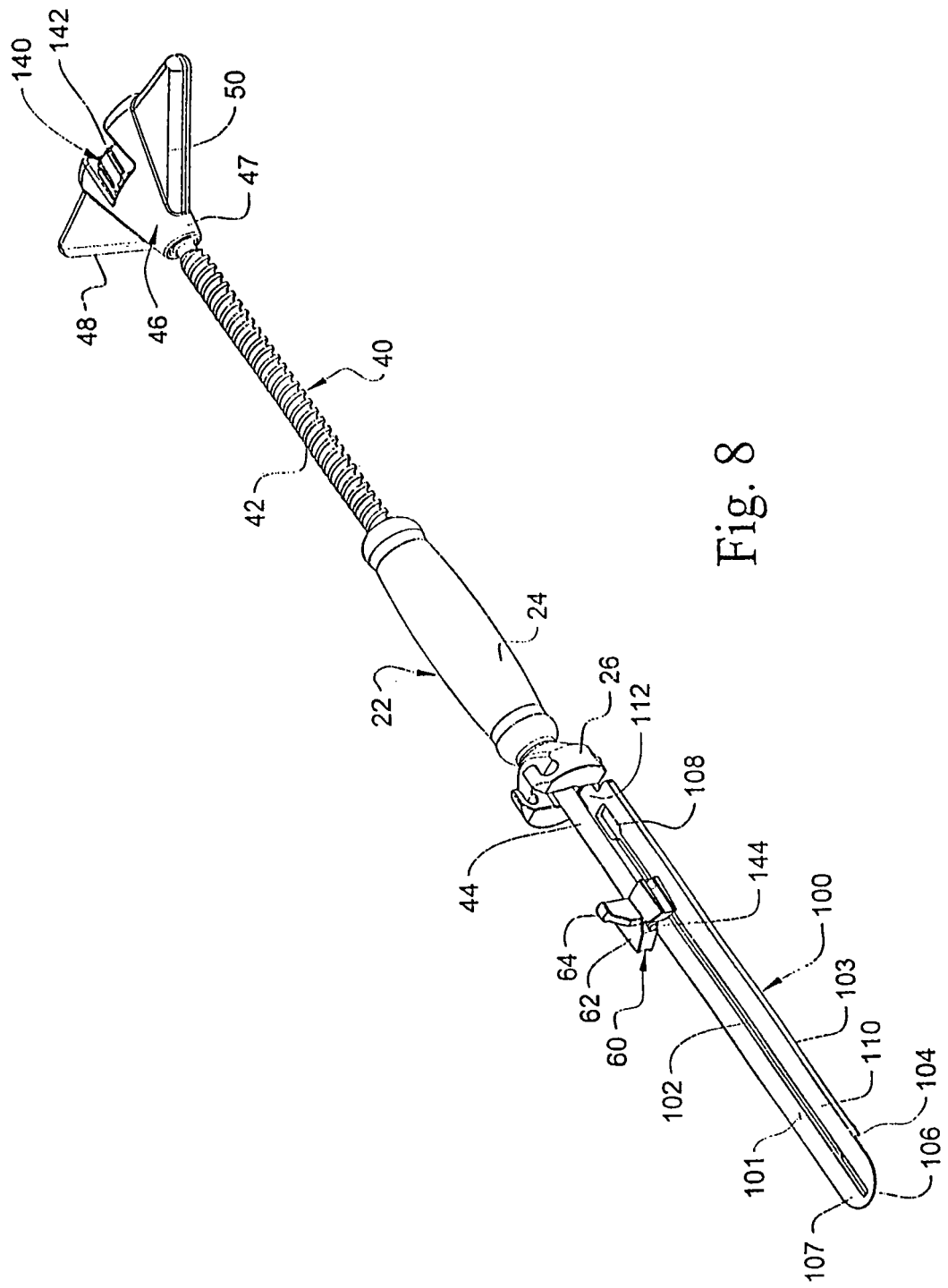
FIG. 8 is a perspective view of the housing, drive member, spreader and lower guide member assembled with an implant holder.

Guide members 100, 120 extend distally from housing 22, and define a path for insertion of an implant between the adjacent bony portions, such as vertebrae 220, 222. As shown in FIG. 8, guide member 100 includes a body 110 extending from a proximal end 112 to a distal end 106. Body 110 can be provided with an elongated guide slot 102 extending therethrough along a central axis of body 110. Guide slot 102 opens along a guide surface 101 and an opposite outer surface 103 of body 110. Guide slot 102 extends from a location adjacent proximal end 112 to a location adjacent distal end 106. Guide slot 102 includes an enlarged proximal end opening 108 for passage of the enlarged outer end of lower wing 66. The remaining proximal portion of guide slot 102 is sized to slidingly receive the body 67 of lower wing 66, but prevents passage of the enlarged outer end of wing 66 therethrough.

Similarly, as shown in FIG. 14, guide member 120 includes a body 134 extending from a proximal end 130 to a distal end 126. Body 134 can be provided with an elongated guide slot 122 extending therethrough along a central axis of body 134. Guide slot 122 opens along a guide surface 121 and opposite outer surface 123 of body 134. Guide slot 122 extends from a location adjacent proximal end 130 to a location adjacent distal end 126. Guide slot 122 includes an enlarged proximal end opening 128 for passage of the enlarged outer end of upper wing 64. The remaining proximal portion of guide slot 122 is sized to slidingly receive the body 65 of upper wing 64, but prevents passage of the enlarged outer end of wing 64 therethrough.

Guide member 100 can be provided with an abutment member 104 adjacent distal end 106 projecting from outer surface 103 for contacting the adjacent bony structure to limit the insertion depth of guide member 100 into the space between the adjacent bony portions. A support member 107 of guide member 100 extends distally from abutment member 104 and into the space between the adjacent bony portions, forming an extension of guide surface 101 and outer surface 103. Guide member 120 can be provided with an abutment member 124 projecting from outer surface 123 adjacent distal end 126 for contacting the adjacent bony portion to limit the insertion depth of guide member 120 into the space between the adjacent bony portions. A support member 127 extends distally from abutment member 124 and into the space between the adjacent bony portions, forming an extension of guide surface 121 and outer surface 123.

When assembled to housing 22, the guide surfaces 101, 121 of guide members 100, 120 are oriented toward one another. Support members 107, 127 can extend along an adjacent surface of the adjacent bony portion to facilitate insertion of the implant 160 into the space between the adjacent bony portions. Support members 107, 127 also contact the adjacent bony portions to distribute a spreading or distraction force thereto. The spreading or distraction force can be applied to the adjacent bony portions by separating guide members 100, 120 as the implant 160 and spreader 60 are distally advanced between guide members 100, 120. Support members 107, 127 further protect the adjacent vertebral endplate as implant 160 is positioned in the space between the adjacent bony portions. Support member 107, 127 can prevent implant 160 from cutting into or becoming engaged with bony structure at the entrance into the space therebetween, and facilitate insertion of implant 160 in the desired position in the space between the adjacent bony portions.

Figure 9:
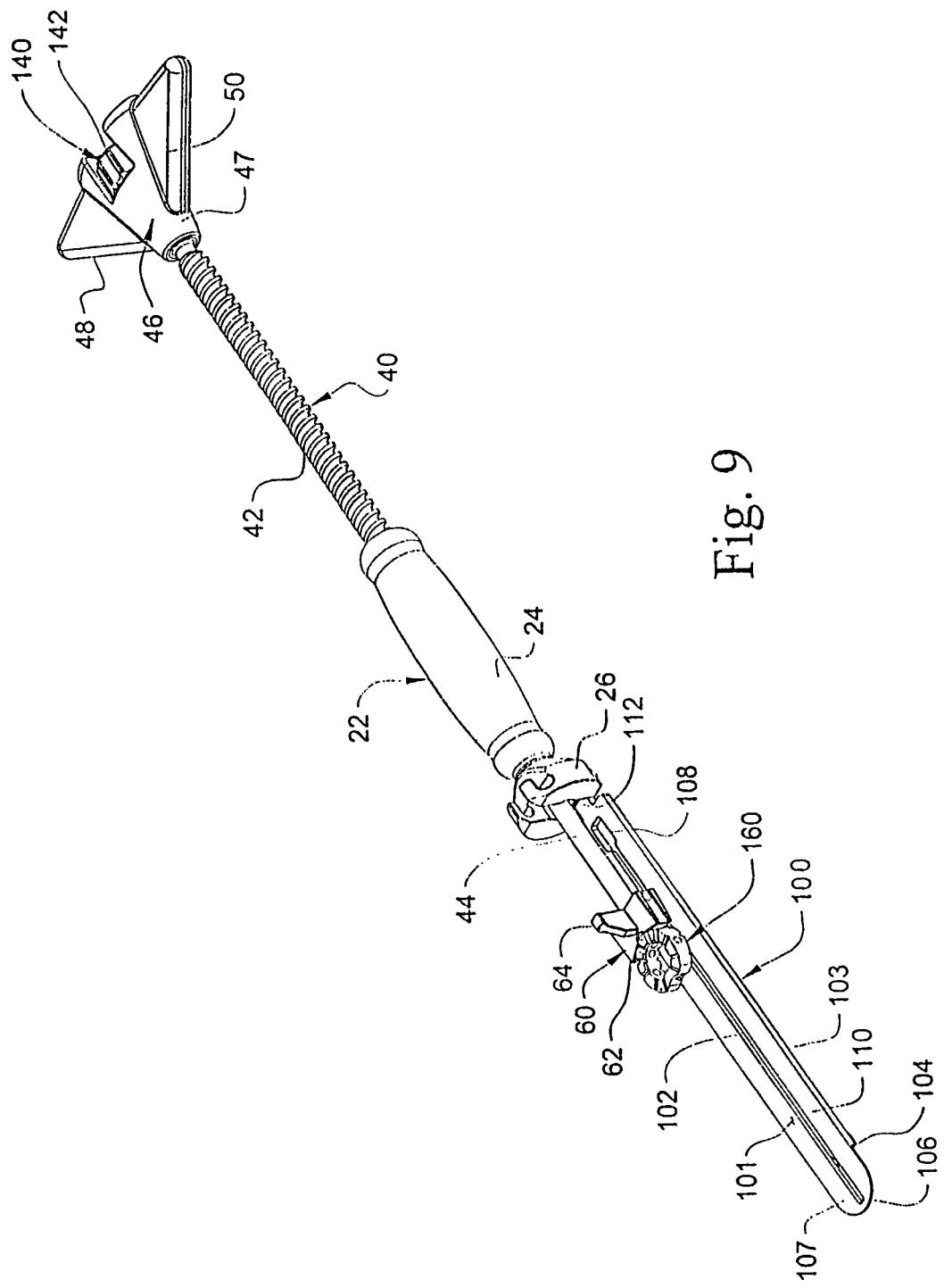
FIG. 9 is a perspective view of the assembly of FIG. 8 with an implant positioned forwardly of the spreader on the lower guide member.

Referring now to FIG. 8, implant holder 140 is shown positioned through passage 54 (FIG. 3) of drive member 40. Implant holder 140 includes an elongated shaft extending from a distal end 144 to an adjustment member 142 at its proximal end. Adjustment member 142 is received in recess 52 (FIG. 3) of handle 46, and can be grasped by the surgeon to rotate the shaft and thus distal end 144 to engage a female threaded hole in implant 160 positioned forwardly of spreader 60, as shown in FIG. 9. Implant holder 140 firmly holds implant 160 against the leading or distal end wall of spreader 60. Other embodiments contemplate other coupling arrangements between distal end 144 and implant 160, including an interference fit, snap fit, ball plunger and groove, or other suitable releasable coupling arrangement.

Figure 10:
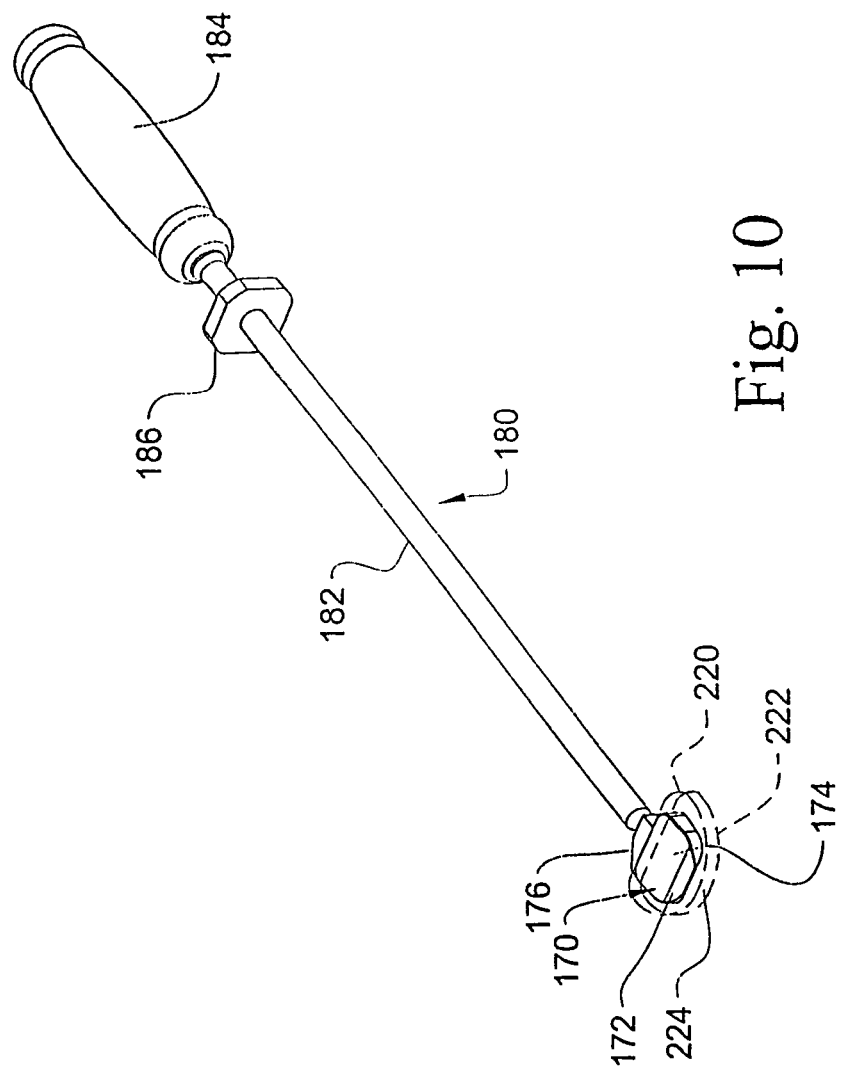
FIG. 10 is a perspective view of a distractor assembly with a distractor head thereof positioned in a spinal disc space.

One procedure employing inserter instrument 20 will be discussed with reference to FIGS. 10-18. In FIG. 10 there is shown distractor head 170 coupled to a distal end of a shaft assembly 180. Distractor head 170 includes a tapered leading end nose 172 to facilitate insertion into disc space 224 between vertebrae 220, 222 when the disc space is collapsed. The body of distractor head 170 tapers to an upper surface 174 and an opposite lower surface (not shown.) The upper and lower surfaces define a distraction height that separates the adjacent vertebral endplates to a corresponding disc space height when distractor head 170 is inserted. Distractor head 170 further includes a proximal flange member 176 for coupling with shaft assembly 180. After insertion of distractor head 170, the disc space height is evaluated to determine if the proper disc space height has been obtained. It is contemplated that a number of distraction heads of various heights can be provided for sequential distraction of disc space 224. If the last inserted distractor head does not provide the desired disc space height, a second distractor head is selected and coupled to shaft assembly 180 for insertion into the disc space. The process is repeated until the disc space height desired has been attained.

Figure 11:
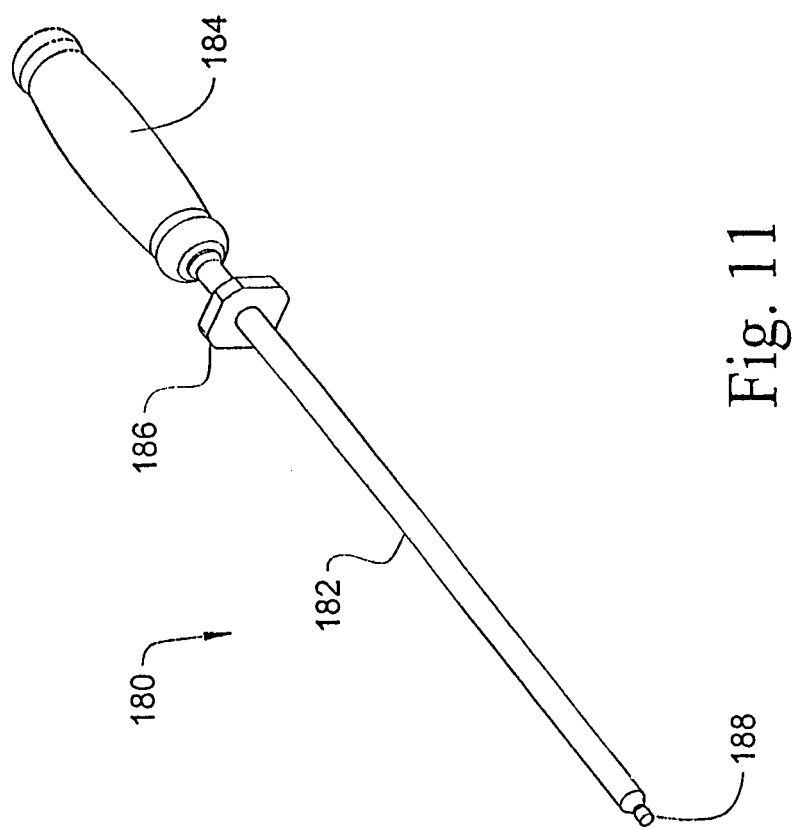
FIG. 11 is a perspective view of a shaft assembly comprising a portion of the distractor assembly of FIG. 10.
Figure 12:
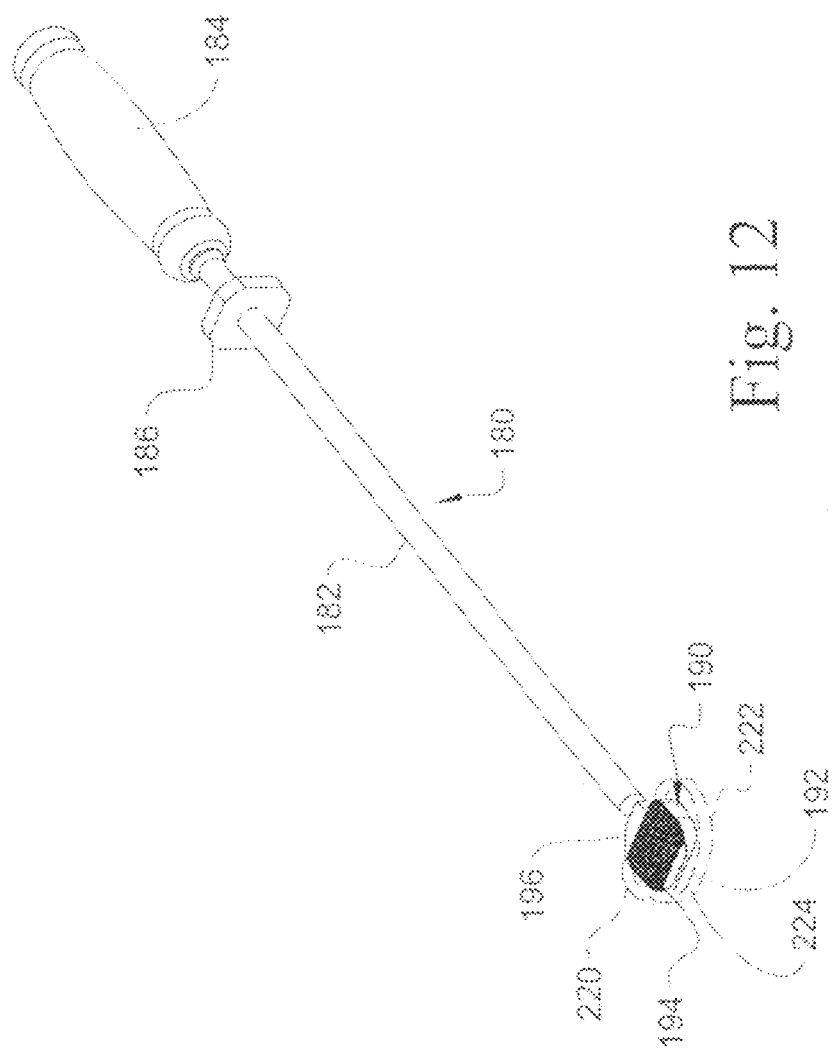
FIG. 12 is a perspective view of a rasp assembly with a rasp head in the spinal disc space and coupled to a distal end of the shaft assembly of FIG. 11.

Further details of shaft assembly 180 are shown in FIG. 11. Shaft assembly 180 includes a shaft 182 extending to a distal coupling end 188. Distal coupling end 188 is removably engageable to distractor head 170 and, as shown in FIG. 12, a rasp head 190. In one embodiment, distal coupling end 188 includes external threads to engage a threaded hole in flange member 176. Other embodiments contemplate other coupling arrangements, including a snap fit, a quick connect coupler, for example. It is also contemplated that shaft assembly 180 can be integrally formed with distractor head 170 or rasp head 190. A handle 184 is provided at the proximal end of shaft 182 to facilitate insertion and withdrawal of the distractor and rasp heads. A collar 186 extends about shaft 182 distally of handle 184 to provide a platform to receive impaction forces for insertion or withdrawal of the distractor or rasp heads from the disc space.

In FIG. 12 there is shown rasp head 190, which is also removably attachable to distal coupling end 188 of shaft assembly 180 at proximal flange member 196. Rasp head 190 includes a tapered leading end nose 192 and a body 194. The upper and lower surfaces of body 194 include roughened surfaces to facilitate rasping of bone material of the adjacent vertebral endplates. Body 194 defines a height between the upper and lower surfaces that corresponds to the height of the last distractor head inserted into the disc space. Thus, it is contemplated that rasp head 190 can be provided in a set of a number of rasp heads with heights corresponding to heights of distractor heads provided in the set.

Figure 13:
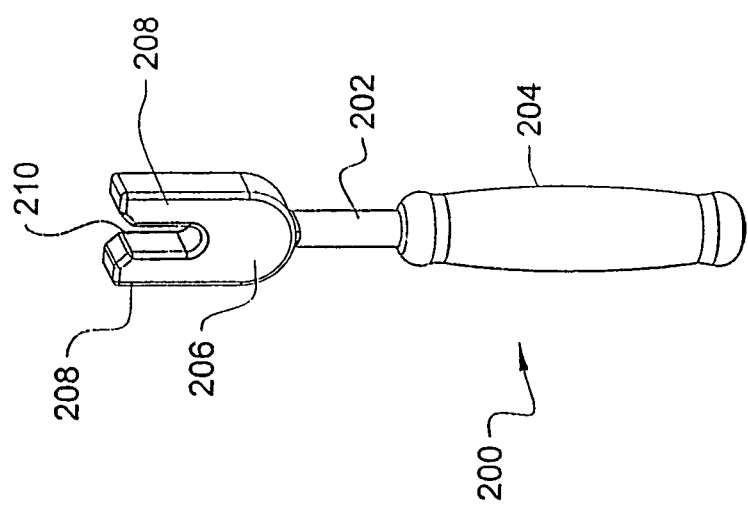
FIG. 13 is a perspective view of a mallet.

In FIG. 13 there is shown a mallet 200, which includes a shaft 202 and a proximal handle 204. An impaction head 206 is provided at the distal end of shaft 202. Impaction head 206 includes a U-shaped recess 210 formed by distally extending arms 208 on each side thereof. Arms 208 are positionable about shaft 182 of shaft assembly 180. Mallet 200 is positioned proximally of collar 186 to deliver an impaction insertion force, or distally of collar 186 to deliver an impaction removal force.

Figure 15:
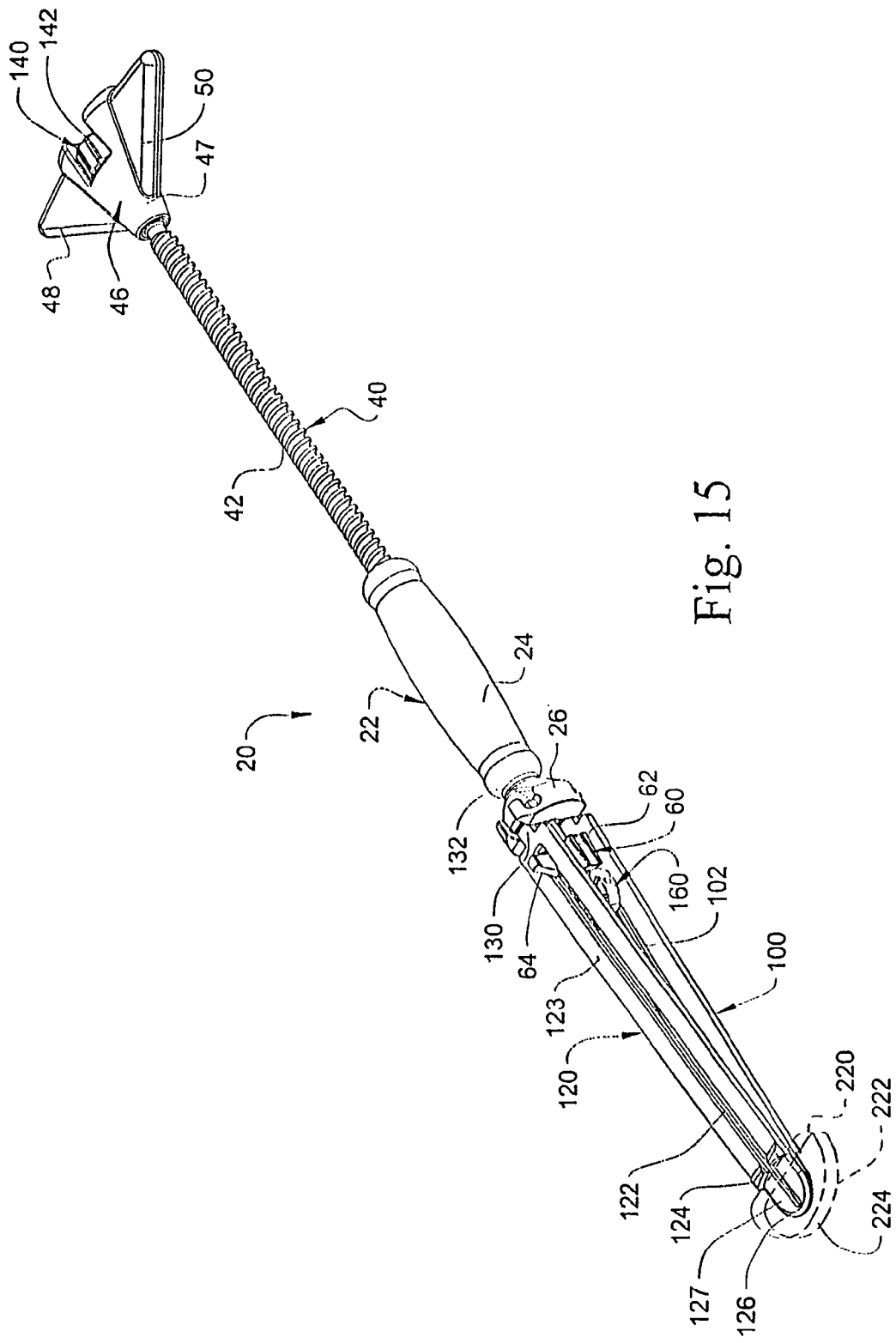
FIG. 15 is a perspective view of the loaded implant inserter instrument positioned for delivery of an implant to the spinal disc space.

After distraction of the disc space with distractor head 170 and preparation of the endplates with rasp head 190, implant 160 can be delivered to the disc space with inserter instrument 20. In FIG. 14, upper guide member 120 is pivoted away from lower guide member 100 to facilitate placement of implant 160 forwardly of spreader 60. Implant holder 140 is then rotated to engage the implant 160 and hold it in place against the leading end wall of spreader 160. If desired, adapter 80 can be mounted to spreader 60 to provide a more distal placement of implant 160 relative to guide members 100, 120 and spreader 60. Drive member 140 is fully retracted or withdrawn proximally relative to housing 22 so that spreader 60 is placed in alignment with enlarged slot portions 108, 128, allowing guide member 100 to be lowered into place about upper wing 64, as shown in FIG. 15.

In one embodiment, it is contemplated that implant 160 is selected from a set of implants having various heights and or angulation between its upper and lower surfaces. The implant of the appropriate height can be selected to provide a height that corresponds to the distractor head providing the desired disc space height during distraction. In this manner, when the implant is inserted, it will fit within the disc space since an indication of its fit has already been provided by the last inserted distractor head.

With the distraction and rasping instruments removed from disc space 224, the implant 160 is loaded into inserter instrument 20. The pivoting coupling arrangement of guide members 100, 120 allows distal ends 106, 126 to be positioned adjacent one another. This provides a low profile arrangement that allows positioning of support members 107, 127 in the disc space 220, even if the disc space has collapsed due to removal of distraction. Abutment members 104, 124 are positioned in contact with the adjacent vertebral bodies, preventing over insertion of guide members 100, 120 into the disc space. In the illustrated embodiment, abutment members 104, 124 are orthogonally oriented to the central axis of the guide members, aligning guide members 100, 120 for implant insertion approach along or parallel to, for example, the saggital or coronal planes in spinal procedures. In another embodiment, abutment members are obliquely oriented to the central longitudinal axis of guide members 104, 124 to facilitate placement of guide members 100, 120 in an approach obliquely oriented to, for example, the sagittal and coronal planes in spinal procedures.

Figure 16:
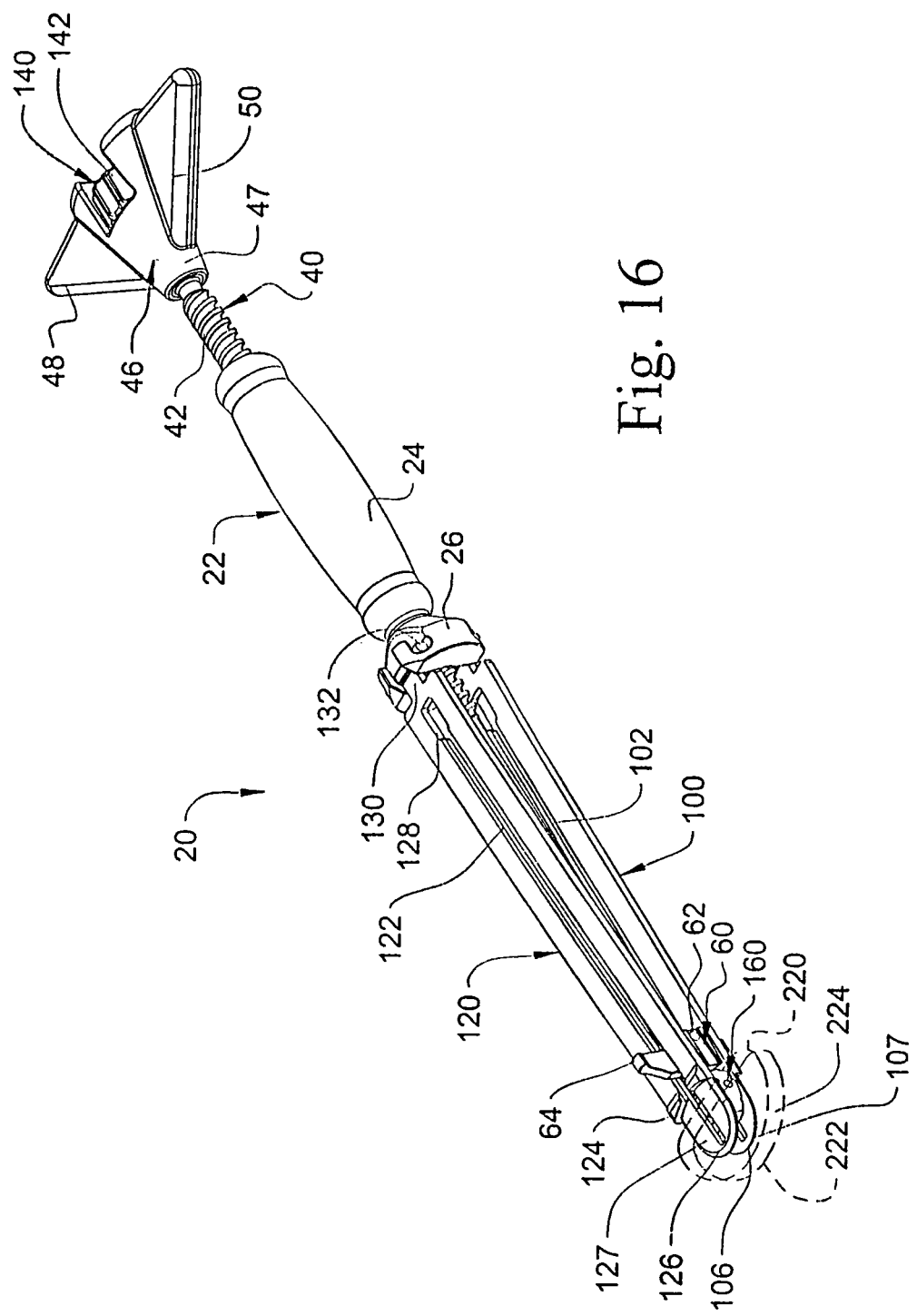
FIG. 16 is a perspective view of the loaded implant inserter instrument with the implant driven distally toward the spinal disc space.

In FIG. 16 implant 160 is advanced distally between guide members 100, 120 by rotating drive member 40 within housing 22, distally advancing drive member 40 and thus spreader 60 and implant 160 along guide members 100, 120. As the implant 160 and spreader 60 are advanced, the guide members 100, 120 are spread apart or separated from one another. This separation causes support members 107, 127 to exert a distraction force on the vertebral endplates, separating vertebrae 220, 222 a sufficient distance to accommodate implant 160 therebetween.

Figure 17:
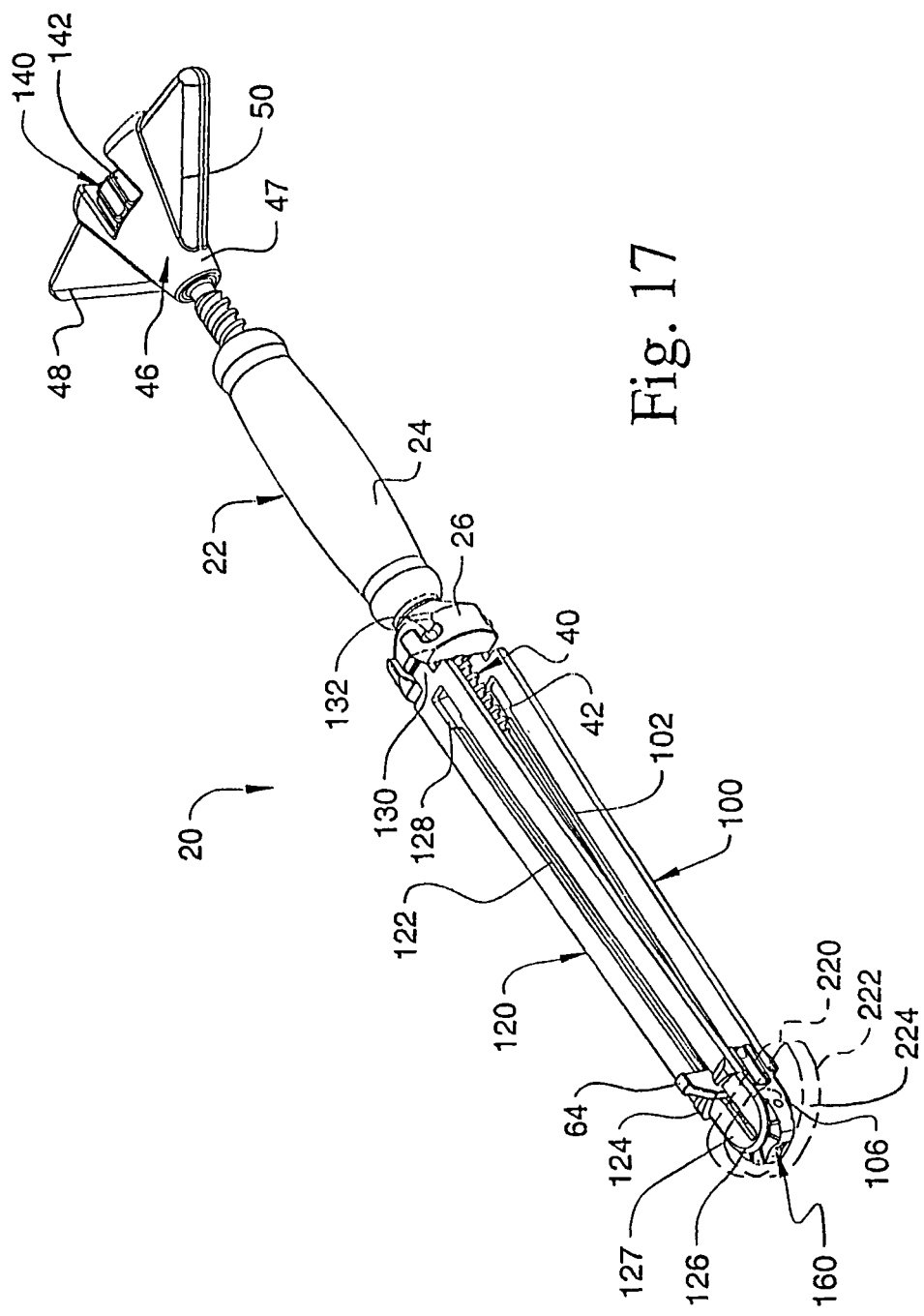
FIG. 17 is a perspective view of the loaded implant inserter instrument with the implant driven into the spinal disc space and the spreader contacting the adjacent vertebral bodies.

In FIG. 17 implant 160 is positioned in the spinal disc space 224. Wings 64, 66 are aligned with abutment members 104, 124 adjacent the vertebral bodies 220, 222, respectively. Support members 107, 127 however, are positioned between the inserted implant 160 and the adjacent vertebral endplate, making withdrawal of inserter 20 from the disc space difficult. Wings 64, 66 each include a distal end wall that tapers proximally along the respective body 65, 67 to the enlarged outer end of the respective wing 64, 66. This allows wings 64, 66 to better conform to the anatomy of vertebrae 220, 222 at the transition between the endplates and the outer surfaces of the vertebral bodies, and prevents the wings 64, 66 from contacting the vertebral bodies before implant 160 is positioned at the desired location in the disc space 224.

Figure 18:
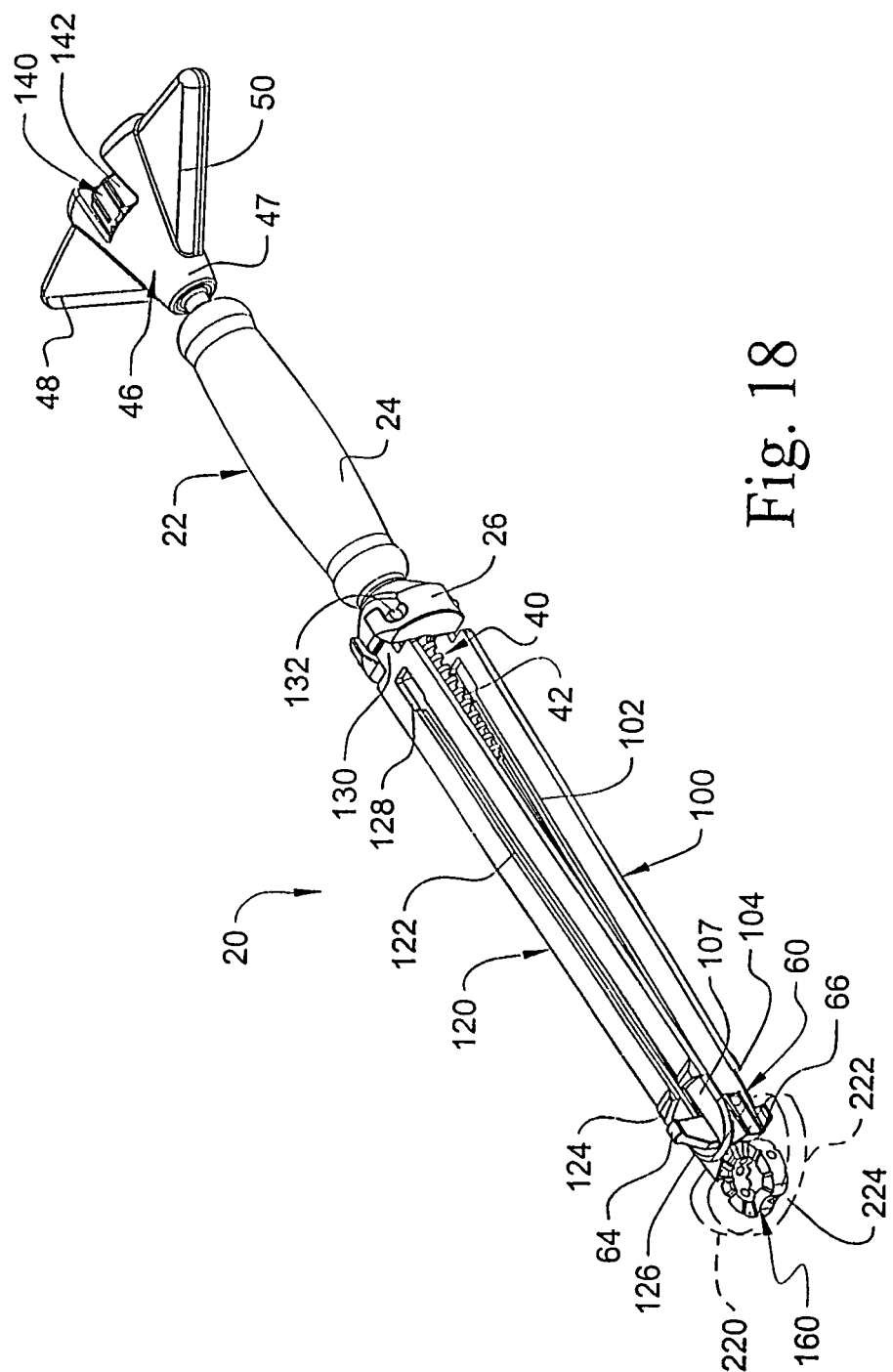
FIG. 18 is a perspective view of the implant inserter instrument with the implant unloaded into the spinal disc space and the spreader advanced to the distal end of the guide member slots to withdraw the guide members from the spinal disc space.

Slots 102, 122 extend through abutment members 104, 124, providing an avenue for further advancement of spreader 60 relative to guide members 100, 120. In FIG. 18, drive member 40 has been rotated to completely displace spreader 60 to the distal ends of slots 102, 122. Since wings 64, 66 contact the adjacent vertebrae 220, 222, spreader 60 cannot advance toward the disc space. Thus, wings 64, 66 act on vertebral bodies 220, 222 to displace guide members 100, 120 proximally, withdrawing support members 107, 227 from the space between implant 160 and the adjacent vertebral endplates. This allows inserter instrument 20 to be readily withdrawn from the operative site without twisting or impaction, which could disrupt implant positioning in the disc space.

As implant 160 is guided between guide members 100, 120 into the space between the adjacent bony portions, the positioning of implant 160 is controlled in the cephalad/caudal directions by contact of guide surfaces 101, 121 with implant 160. Guide surfaces 101, 121 align implant 160 with the space between the adjacent bony portions. The lateral positioning of implant 160 along guide members 100, 120 is controlled by engagement of implant holder 140 with implant 160 so that implant 160 does not slip out from between guide members 100, 120, where it might contact or damage tissue, nerves, vasculature or other tissue structures adjacent the bony portions on the approach to the space therebetween. Wings 64, 66 of spreader 60 extend through slots in the upper and lower guide members, and are centrally located to minimize intrusion into the surrounding tissue. The spreader and guide member arrangement further facilitates rapid loading and unloading of an implant between the guide members.

The instruments discussed herein can protect the adjacent tissue and vasculature from the implant during insertion by preventing the implant 160 and spreader 60 from twisting and moving outside the guide path during insertion. The instruments further protect the bony structures between which the implant is inserted during insertion, and facilitate withdrawal of the implant after it is positioned in the space between the bony structures. Furthermore, the instruments can be adapted to guide insertion of implants of various heights and various taper angles, and to provide varying spacing between adjacent bony portions customized to fit the particular implant. The instruments include a low profile in the operative space, facilitating visualization and placement of additional instruments in the operative approach to the bony structures. The instruments are simple to disassemble, allowing for cleaning and use of selected guide members from a set of guide members, providing convenience and flexibility to the surgeon during the surgical procedure.

The implants discussed herein can be fusion implants adapted to permit fusion of the adjacent bony portions. Such fusion implants can be packed with bone growth promoting material and/or therapeutic agents. The implants discussed herein can also be any spinal implant movable between guide members 100, 120, such as interbody spacers, artificial disc components or devices, or other implants desired to be positioned between adjacent bony portions.

While the invention has been illustrated and described in detail in the drawings and foregoing description, the same is to be considered as illustrative and not restrictive in character. All changes and modifications that come within the spirit of the invention are desired to be protected.

The invention claimed is:

1. A system, comprising:
    a spinal implant positionable in a space between adjacent bony portions;
    a surgical instrument for delivering said spinal implant to the space, said surgical instrument including:
        a housing;
        a pair of opposing guide members extending distally from said housing, said pair of guide members each including an elongated body with an outer surface and an opposite inner surface facing the inner surface of the other guide member with said spinal implant being positionable between said inner surfaces, at least one of said guide members further including a distally extending elongated slot extending continuously between and opening through said inner surface and said outer surface of said at least one guide member;
        a central body between said pair of guide members, said central body including at least one wing extending therefrom slidingly received in said slot of said at least one guide member; and
        a drive member extending from said central body that is operable to distally advance said central body and said spinal implant between said guide members.

2. The system of claim 1, wherein said housing includes a coupling portion and a drive member engaging portion extending proximally from said coupling portion, said drive member engaging portion and said coupling portion including a passage extending therethrough for receiving said drive member.

3. The system of claim 1, wherein said drive member includes a shaft threadingly engaged in a passage of said housing and a handle at a proximal end of said shaft.

4. The system of claim 3, further comprising an implant holder extending through said drive member and said central body, said implant holder including an adjustment knob at a proximal end thereof and a distal end extending distally of said central body for engagement with said spinal implant.

5. The system of claim 1, wherein said pair of guide members each include an abutment member adjacent said distal end thereof, said abutment member projecting from said outer surface of said respective guide member.

6. The system of claim 5, wherein said abutment members are each orthogonally oriented relative to a central axis of said respective guide member.

7. The system of claim 5, wherein said slot extends through said abutment member of said at least one guide member.

8. The system of claim 5, wherein each of said guide members includes a support member extending distally of said abutment member thereof, said support members being positionable in the space between the adjacent bony portion with said abutment members in contact with respective ones of the adjacent bony portions.

9. The system of claim 1, wherein:
    said housing comprises a coupling portion including a pair of upper fingers each defining a proximally opening receptacle and a pair of lower fingers each defining a proximally opening receptacle; and
    each of said guide members includes a proximal end adapted to be positioned between a corresponding pair of said upper and lower fingers, said guide members each further including a crossbar rotatably and removably received in said receptacles defined by said corresponding pair of fingers.

10. The system of claim 1, wherein said at least one wing includes a body extending from said central body and an enlarged outer end, said enlarged outer end being sized to capture said wing in said slot of said at least one guide member in which said wing is received.

11. The system of claim 10, wherein said slot includes an enlarged proximal end opening adapted to permit passage of said enlarged outer end of said wing therethrough.

12. The system of claim 1, wherein said inner surfaces are planar.

13. The system of claim 1, wherein said slot includes a distal end located proximally of a distal end of said at least one guide member.

14. The system of claim 1, further comprising a distractor including a distractor head extending from a distal end of a shaft, said distractor head including a height extending between upper and lower surfaces of said distractor head to separate the adjacent bony portions to a desired disc space height when said distractor head is positioned between said adjacent bony portions.

15. The system of claim 14, further comprising a rasp head, wherein said distractor head and said rasp head are each removably engageable with said distal end of said shaft.

16. The system of claim 1, wherein said spinal implant includes bone growth material.

17. A system comprising:
a spinal implant positionable in a space between adjacent bony portions;
an inserter instrument including:
a housing;
pair of opposing guide members extending distally from said housing, said pair of guide members each including an elongate body with an outer surface and an opposite inner surface facing the inner surface of the other guide member, each of said guide members including an elongated slot extending between and opening through said inner surface and said outer surface thereof with said spinal implant being positionable between said inner surfaces, each of said guide members further including an abutment member adjacent a distal end of each guide member with said slots each extending continuously between and opening through inner and outer surfaces of said abutment members, each of said abutment members being positionable in contact with at least one of the adjacent bony portions;
a central body between said pair of guide members, said central body including a to surface and an opposite bottom surface each having a wing extending therefrom, said wings facing away from one another such that said wings are slidingly received in said slots; and
drive member extending proximally from said central body through said housing, said drive member being operable to advance said central body and said spinal implant distally between said guide members.

18. The system of claim 17, wherein said slot of said at least one guide member includes a distal end between said abutment member and said distal end of said at least one guide member.

19. A system comprising:
a spinal implant positionable in a space between adjacent bony portions;
an inserter instrument including:
a housing;
a pair of opposing guide members coupled to said housing, each of said pair of guide members including a body with an outer surface and an opposite guide surface, wherein said guide surfaces face one another and at least one of said guide members includes an elongated slot extending continuously between and opening through said outer surface and said guide surface thereof, said spinal implant being positionable between said guide surfaces of said guide members;
a spreader positioned between said pair of guide members, said spreader including a central body and at least one wing extending therefrom, said at least one wing being slidingly received in said at least one slot of said at least one guide member; and
a drive member extending along an axis, said drive member being coupled to said spreader and including a shaft threadingly engaged in a passage of said handle such that clockwise rotation of said shaft causes said spreader to translate along said axis in a first direction and counterclockwise rotation of said shaft causes said spreader to translate along said axis in an opposite second direction,
wherein said at least one wing includes a body extending from said central body and an enlarged outer end, said enlarged outer end being sized to capture said wing in said slot of said at least one guide member.

20. The instrument of claim 19, wherein said guide surfaces are planar and said at least one slot includes an enlarged proximal end opening adapted to permit passage of said enlarged outer end of said wing therethrough.

* * * * *